(12) United States Patent
Kleinschmidt

(10) Patent No.: US 7,487,776 B2
(45) Date of Patent: Feb. 10, 2009

(54) DEVICE WITH AN ANESTHESIA RESPIRATION SYSTEM AND AN ABSORBER

(75) Inventor: Lothar Kleinschmidt, Krummesse (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 817 days.

(21) Appl. No.: 11/058,624

(22) Filed: Feb. 15, 2005

(65) Prior Publication Data

US 2005/0235994 A1  Oct. 27, 2005

(30) Foreign Application Priority Data

Apr. 24, 2004  (DE)  .................. 10 2004 020 133

(51) Int. Cl.
*A61M 11/00* (2006.01)
(52) U.S. Cl. .................................. 128/205.12
(58) Field of Classification Search ............ 128/205.12, 128/205.24, 207.12, 204.18, 204.26, 205.13
See application file for complete search history.

(56) References Cited

U.S. PATENT DOCUMENTS

| | | | | |
|---|---|---|---|---|
| 3,707,965 | A | * | 1/1973 | Guzay .................... 128/205.28 |
| 3,830,632 | A | * | 8/1974 | Guzay ....................... 422/120 |
| 4,171,962 | A | * | 10/1979 | Kippel et al. ................ 96/416 |
| 4,353,366 | A | * | 10/1982 | Bickford ................ 128/205.12 |
| 4,991,576 | A | * | 2/1991 | Henkin et al. .......... 128/203.28 |
| 5,743,257 | A | * | 4/1998 | Koehler et al. ......... 128/205.24 |

FOREIGN PATENT DOCUMENTS

| | | |
|---|---|---|
| DE | 197 29 739 | 1/1999 |
| EP | 0 122 301 | 10/1984 |

* cited by examiner

*Primary Examiner*—Steven O Douglas
(74) *Attorney, Agent, or Firm*—McGlew & Tuttle, P.C.

(57) ABSTRACT

A quick connection system between an anesthesia respiration system and an absorber has a gas-tight connection between the anesthesia respiration system and the absorber. The absorber (1) has a concentrically arranged gas inlet opening (8) and a gas outlet opening (9) on its front side (4) for this purpose, as well as a guide plate (3) that can be pushed into an absorber mount at the anesthesia respiration system. Centering notches (11, 12), which engage a centering pin at the absorber mount, are provided at the guide plate (3) in the direction of pushing in.

14 Claims, 6 Drawing Sheets

DEVICE WITH AN ANESTHESIA RESPIRATION SYSTEM AND AN ABSORBER

CROSS REFERENCE TO RELATED APPLICATIONS

This application claims the benefit of priority under 35 U.S.C. § 119 of DE 10 2004 020 133.1 filed Apr. 24, 2004, the entire contents of which are incorporated herein by reference.

FIELD OF THE INVENTION

The present invention pertains to a device with an anesthesia respiration system and an absorber that can be connected with the anesthesia respiration system via a quick connection system.

BACKGROUND OF THE INVENTION

A device of this type has become known from EP 122 301 A1. Anesthesia respiration systems must be able to be used for different modes of operation, and the switchover between the mode of operation shall take place in a simple manner and without operating errors. In addition, nonrepairable items, for example, the carbon dioxide absorber, shall be able to be replaced in a simple manner and rapidly without respiration being compromised. The absorber is arranged in the prior-art anesthesia respiration system in the expiration branch and is connected with switchover elements, which inevitably interrupt the flow of gas in the breathing gas circuit when the absorber is removed and establish separate breathing branches. Quick connection elements, which are designed as lockable plug type connections, are provided for inserting and releasing the absorber.

The absorber has such a design that connecting branches acting as a gas inlet opening and a gas outlet opening are arranged on the front side of a cuboid absorber housing. The drawback of the prior-art absorber design is that the connecting branches must be exactly aligned with the corresponding connection holes when the absorber is inserted into the anesthesia respiration system. Since the absorber is located on the underside of the anesthesia respiration system, the connection holes are not in the user's direct field of vision.

An absorber with a cylindrical housing and concentrically arranged gas inlet and gas outlet can be handled better. An absorber of the type mentioned appears, for example, from DE 197 29 739 C2.

The corresponding connection elements must be placed aligned on one another for a gas-tight connection between the absorber and the anesthesia respiration system in case of this design as well, and larger tolerances may become established due to the manufacture in the connection area between the absorber and the anesthesia respiration system. This happens especially if the absorbers are manufactured as disposable articles and larger tolerances must be allowed for quick connection components at the absorber housing for production technical and cost reasons. Leakage will develop if the absorber tilts in relation to the anesthesia respiration system during mounting.

SUMMARY OF THE INVENTION

The basic object of the present invention is to improve a device of the type mentioned such that the quick connection system between the anesthesia respiration system and the absorber makes possible a gas-tight connection in a simple manner.

According to the invention, a device is provided with an anesthesia respiration system and an absorber that can be connected with the anesthesia respiration system via a quick connection system. The absorber has a concentrically arranged gas inlet opening and gas outlet opening on the front side of an absorber housing as well as a guide plate which can be pushed into an absorber mount at the anesthesia respiration system. A centering notch is provided on the front side of the guide plate in the direction of pushing in. A centering pin, which engages the centering notch and fixes the guide plate in an end position, is fastened to the absorber mount.

The advantage of the present invention is essentially that the centering notch, which is pushed against the centering pin on the absorber mount, is provided on the front side of the guide plate, which is arranged at the absorber and is pushed into an absorber mount at the anesthesia respiration system. When the guide plate is inserted into the absorber mount, only pre-centering of the absorber is carried out, because a greater clearance between the guide plate and the absorber mount must be allowed because of the path of displacement in order for the guide plate and the absorber mount to be tilted in relation to one another.

The final fixation is achieved by means of the centering pin at the absorber mount, which engages the centering notch on the front side of the guide plate and acts as a stop for the guide plate, so that the guide plate assumes an exactly defined position in relation to the anesthesia respiration system.

Two centering notches arranged offset by 180° are advantageously provided at the guide plate. The absorber can thus be pushed into the absorber mount without observing a preferred position.

It is useful to provide the centering notches with wedge-shaped wall surfaces in order for the guide plate to be able to be centered by the centering pin without an angular offset and in order for the gas channels to be connected between the absorber and the anesthesia respiration system to be located one above the other in an aligned manner.

An alternative embodiment of a centering pin advantageously has an upper part, which can perform a stroke movement, is under spring tension and engages correspondingly designed locking grooves within the centering notches. A locking function is thus achieved by the upper part snapping into the corresponding locking groove in the stop position of the guide plate.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
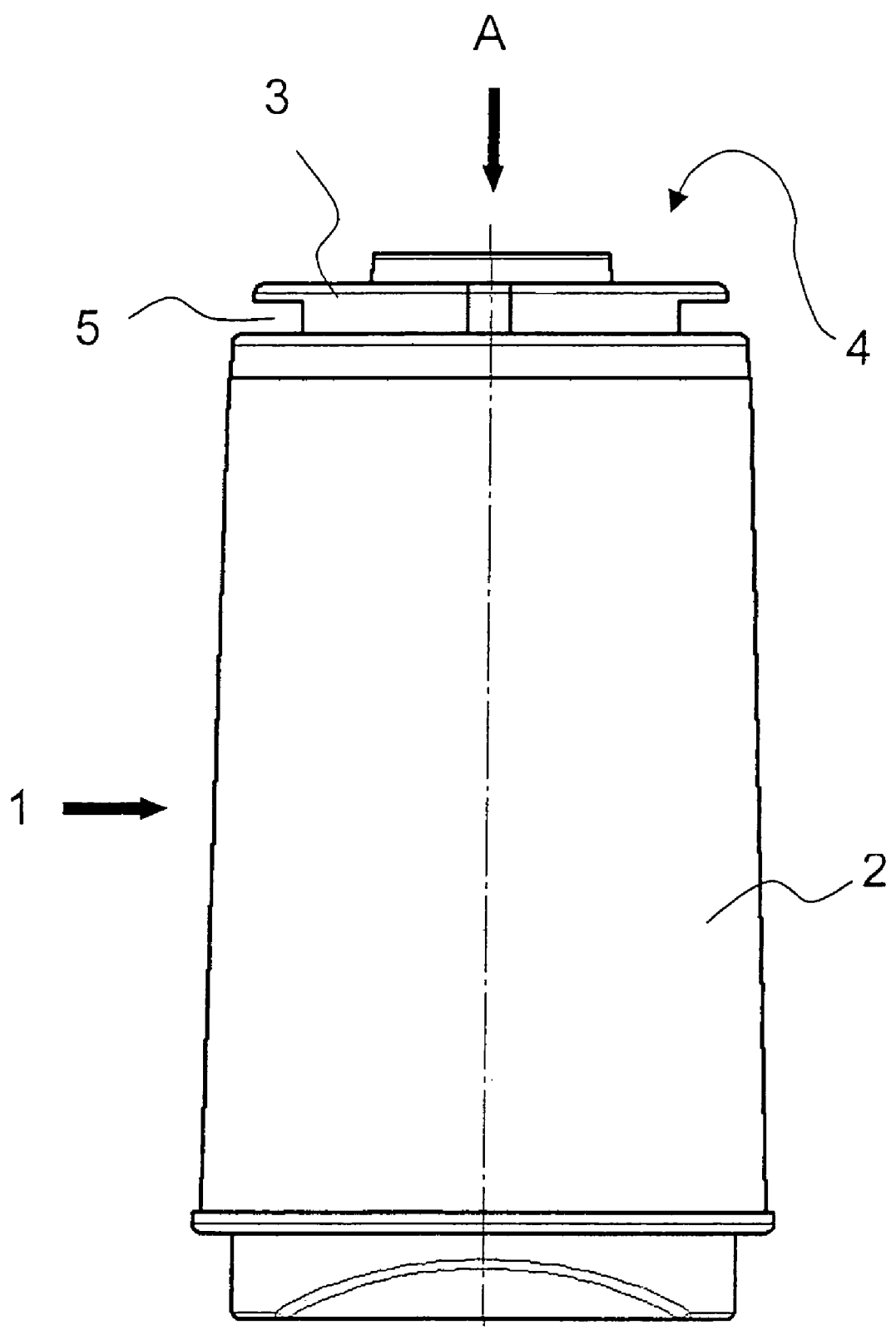
FIG. 1 is a side view of the absorber.

Referring to the drawings in particular, FIG. 1 shows the side view of an absorber 1, which has a guide plate 3 on the anterior front side 4 of an absorber housing 2. A circular groove 5 is located between the front side 4 and the guide plate 3.

Figure 2:
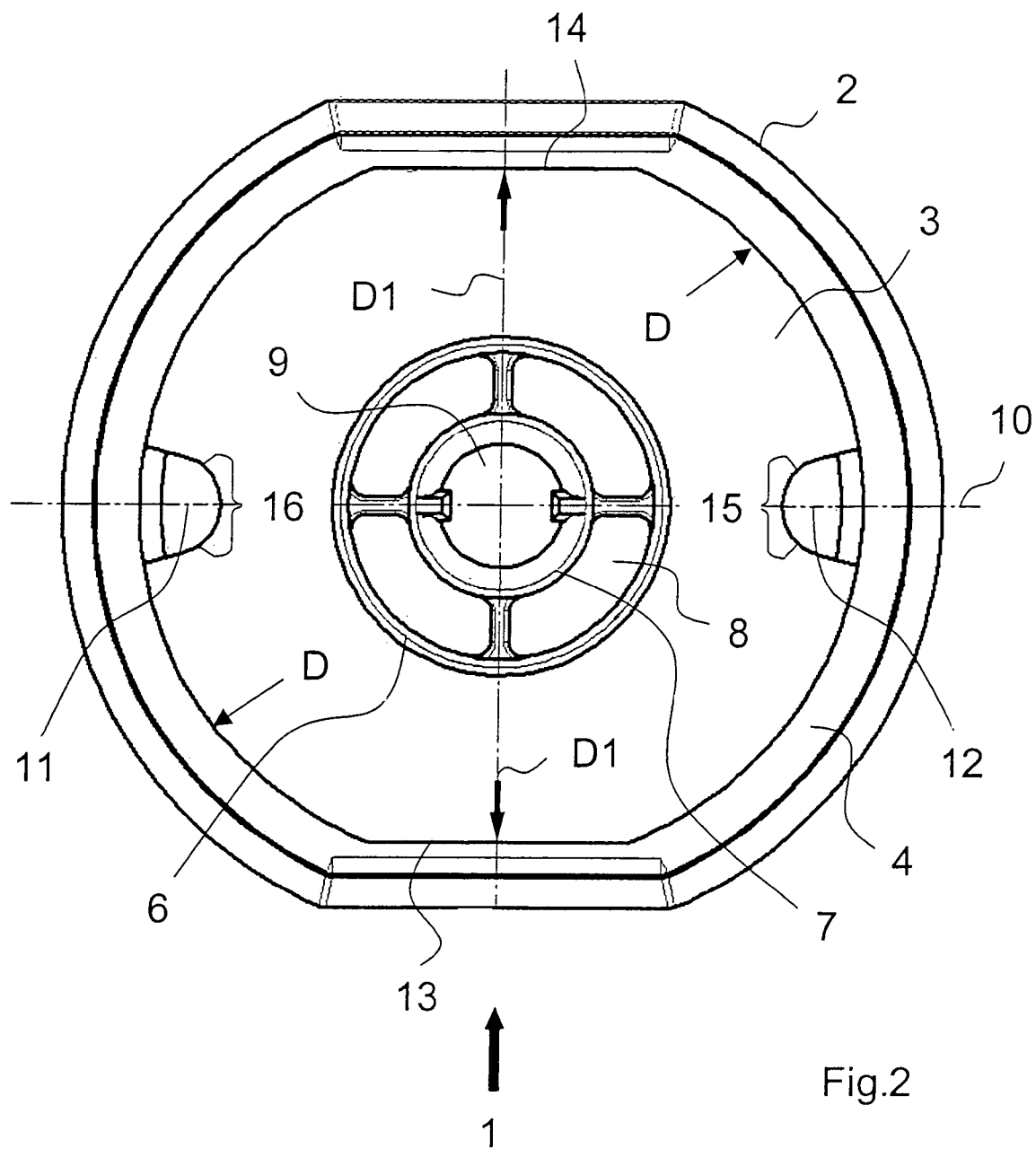
FIG. 2 is a top view of the absorber housing in direction of view A according to FIG. 1.

FIG. 2 shows a top view of the absorber housing 2 in direction of view A according to FIG. 1. An outer sealing crater 6 and an inner sealing crater 7, which define a gas inlet opening 8 and a gas outlet opening 9, are located in the middle of the guide plate 3. The gas channels 8, 9 are arranged concentrically with one another. Along an axis of symmetry 10, the guide plate 3 has two centering notches 11, 12 arranged offset by 180° in relation to one another. In parallel to the axis of symmetry 10, the guide plate 3 has flattened lateral surfaces 13, 14, which reduce the diameter of the guide plate 3, at right angles to the axis of symmetry 10, to the value D 1 compared with the circle diameter D. The centering notches 11, 12 have wall surfaces 15, 16 extending in a wedge-shaped pattern.

Figure 3:
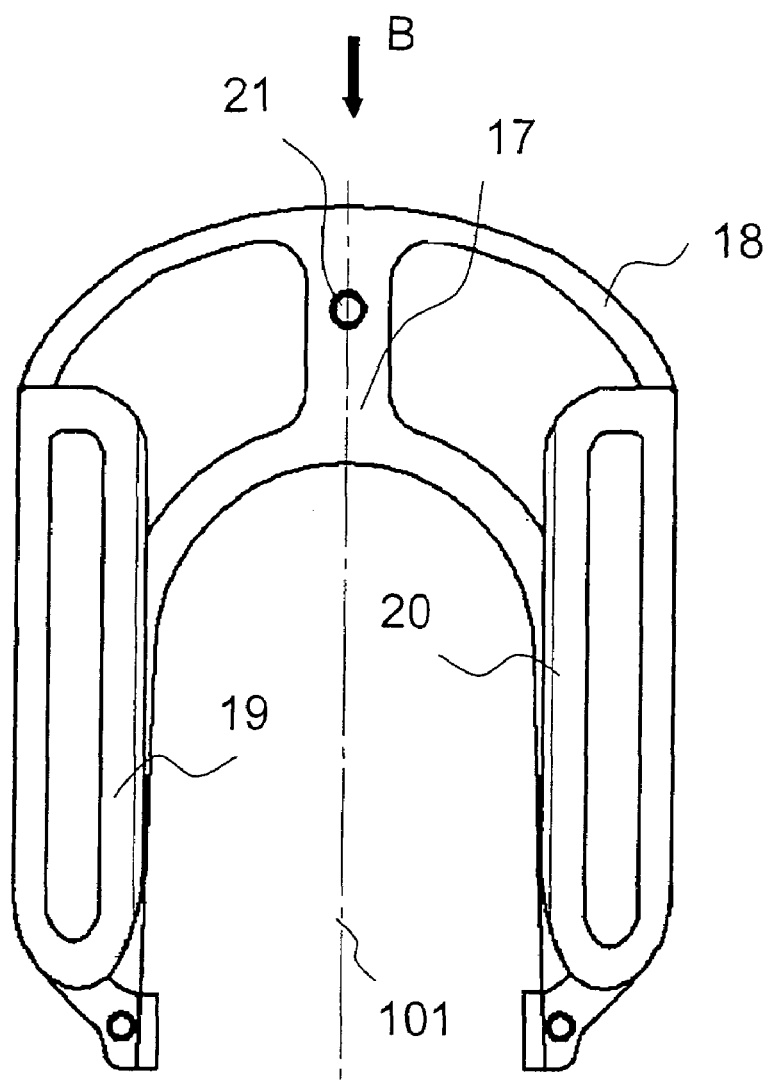
FIG. 3 is an absorber mount.
Figure 4:
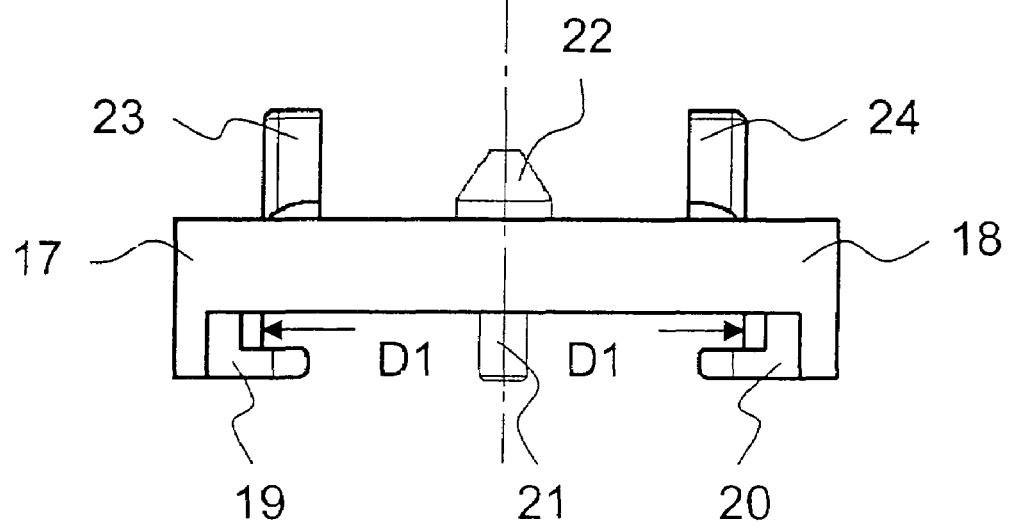
FIG. 4 is the absorber mount in direction of view B according to FIG. 3.

FIG. 3 shows an absorber mount 17, which is located at an adapter plate 18 of an anesthesia respiration system, which is not shown in greater detail. A centering pin 21 is fastened on the top side of the absorber mount 17, aligned with an axis of symmetry 101. The absorber mount 17 has side parts 19, 20 bent over in a U-shaped pattern. FIG. 4 shows the absorber mount 17 with the adapter plate 18 in direction of view B according to FIG. 3. A locking bolt 22 and two bearing blocks 23, 24 connected with the adapter plate 18 are located on the opposite side of the centering pin 21. The width D 1 of the absorber mount 17 in the area of the side parts 19, 20 corresponds to the diameter D 1 of the guide plate 3 in the area of the lateral surfaces 13, 14.

To insert the absorber 1 into the absorber mount 17, the guide plate 3 is pushed into the side parts 19, 20 along the lateral surfaces 13, 14 until one of the centering notches 11, 12 comes into contact with the centering pin 21. For reasons of handling, the clearance between the absorber mount 17 and the lateral surfaces 13, 14 of the guide plate 3 is selected to be such that a certain rotary movement is possible between the absorber 1 and the absorber mount 17 to prevent the guide plate 3 from tilting within the absorber mount 17. The wall surfaces 15, 16 of the centering notches 11, 12 are bent at an angle such that the centering pin 21 is in contact with the wall surfaces 15, 16 in the end position of the absorber 1, and the axis of symmetry 10 of the absorber 1 and the axis of symmetry 101 of the absorber mount 17 are thus caused to coincide.

Figure 5:
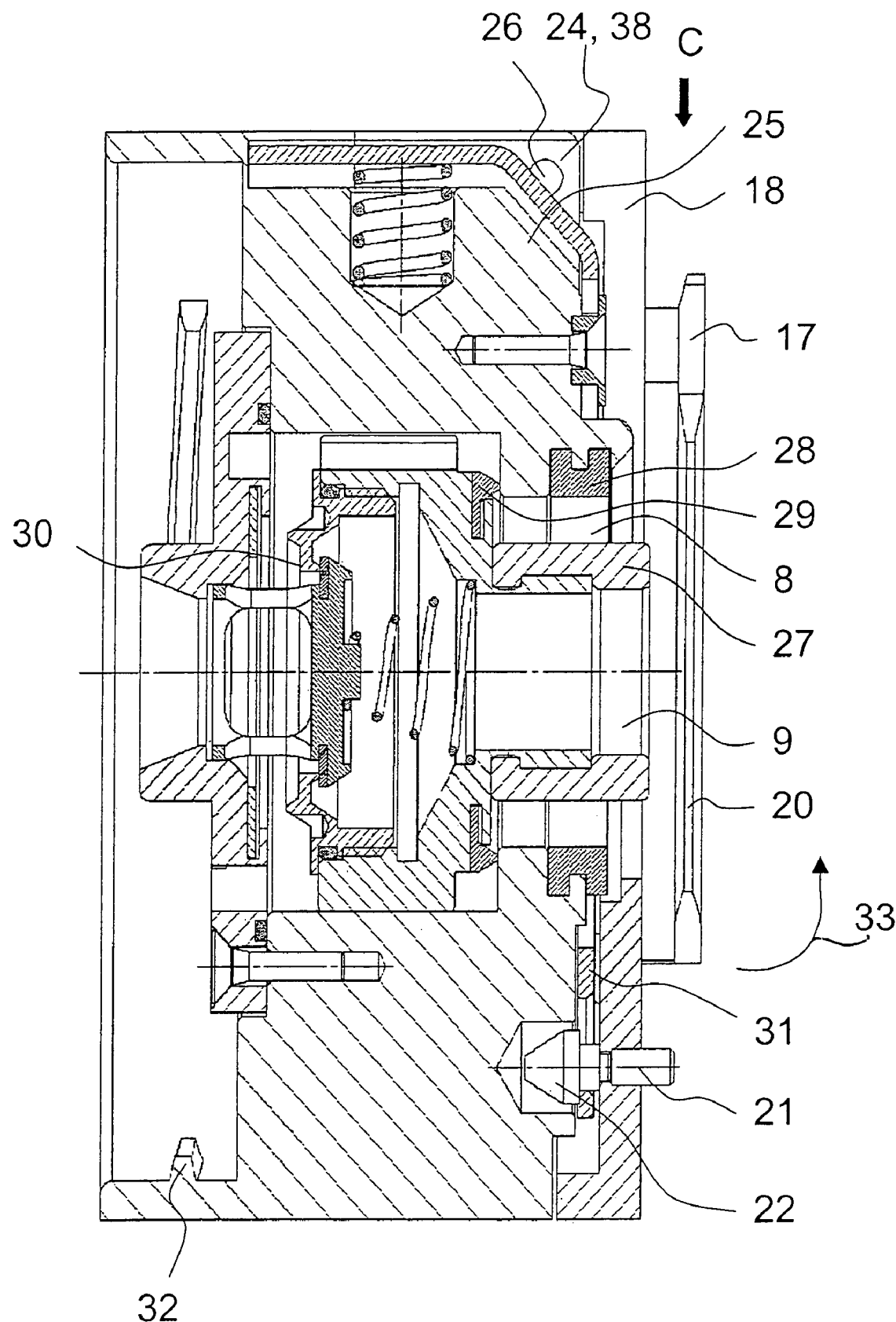
FIG. 5 is a longitudinal section of a connection head for the absorber.

FIG. 5 illustrates a longitudinal section of a connection head 25 for the absorber 1.

The adapter plate 18 is connected with the connection head 25 pivotably around a pin joint 26 via bearing blocks 24, 38. The bearing block 23, FIG. 4, likewise has a pin joint, but it is not recognizable in the sectional view in FIG. 5. A longitudinally displaceable unlocking plate 31 fixes the locking bolt 22 at the connection head 25. The gas connection is established between the absorber 1 and the connection head 25 via profile packings 27, 28, an inner profile packing 27 being in contact with the inner sealing crater 7 and an outer profile packing 28 with the outer sealing crater 6.

With the absorber 1 inserted, the profile packing 27 is pressed inwardly, as a result of which flow valves 29, 30 are opened and a gas connection is established between the absorber 1 and an anesthesia respiration system, not shown specifically in FIG. 5. The connection head 25 is connected with the anesthesia respiration system via a bayonet catch 32.

To insert the absorber 1, the stop bolt 22 is unlocked by displacing the unlocking plate 31 and the adapter plate is pivoted around the pin joint 26 along arrow 33. The absorber 1 is pushed into the absorber mount 17 in the direction of arrow C until one of the centering notches 11, 12 comes into contact with the centering pin 21. The adapter plate 18 is then pivoted back until the unlocking plate 3 will again lock the stop bolt 22.

Figure 6:
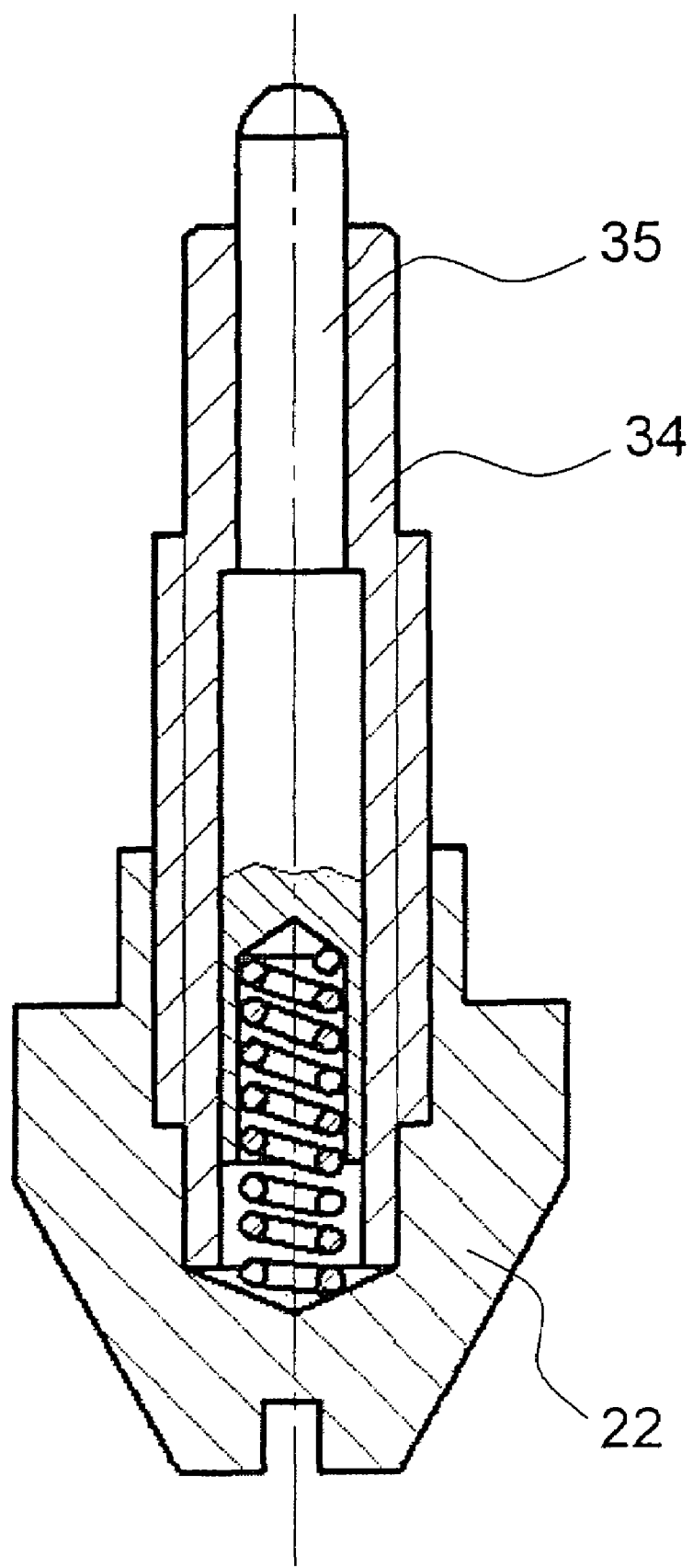
FIG. 6 is an alternative embodiment of a centering pin.
Figure 7:
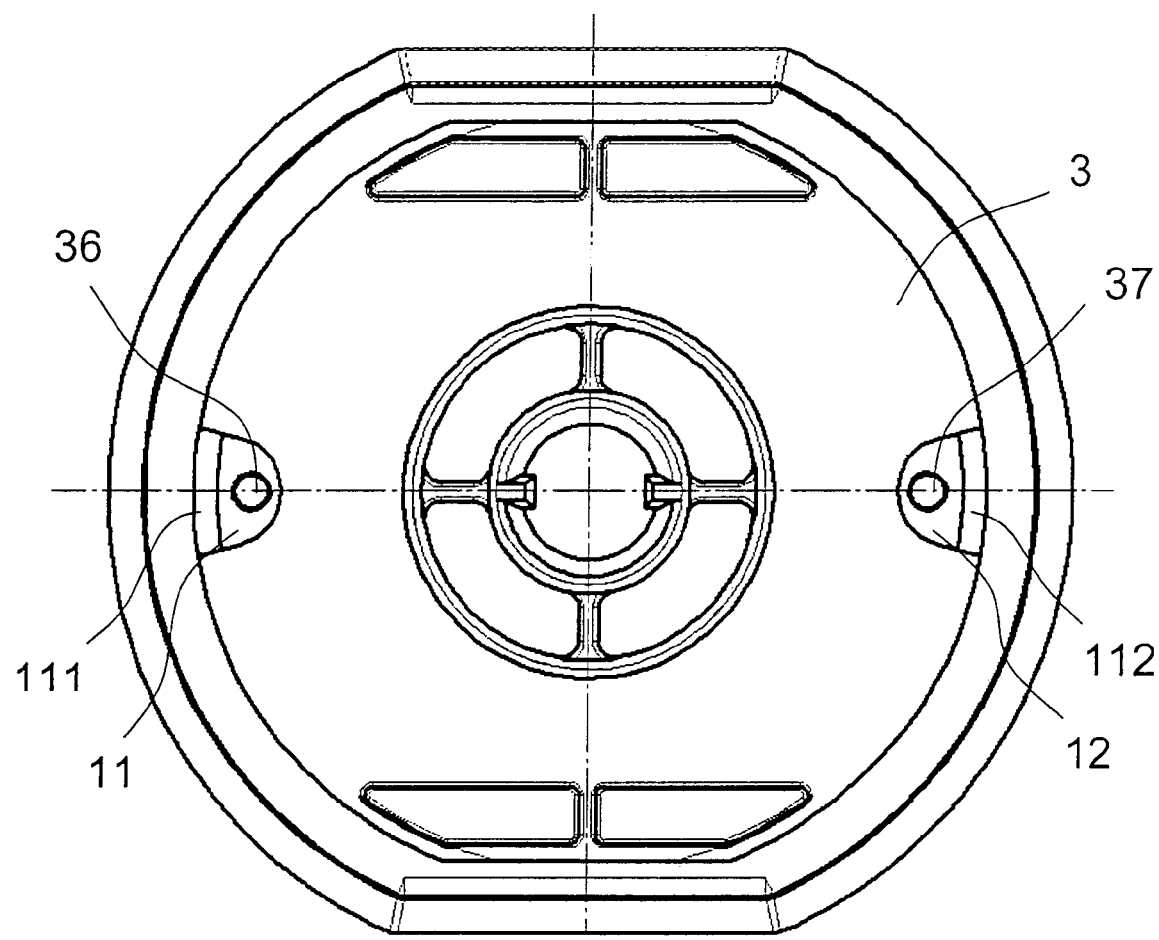
FIG. 7 is an alternative embodiment of an absorber with locking grooves within the centering notches.

FIG. 6 shows an alternative centering pin 34, which has an upper part 35 fixed in a spring-movable manner. The upper part 35 is dimensioned such that it engages locking grooves 36, 37 in the area of the centering notches 11, 12, as can be determined from FIG. 7. The absorber 1 has entry bevels 111 and 112 to introduce the upper part 35 into the locking grooves 36 and 37.

While specific embodiments of the invention have been shown and described in detail to illustrate the application of the principles of the invention, it will be understood that the invention may be embodied otherwise without departing from such principles.

What is claimed is:

1. An anesthesia respiration system to absorber connection device, comprising:
    an absorber for connecting with the anesthesia respiration system, the absorber having an absorber housing, with a gas inlet opening concentrically arranged relative to a gas outlet opening on a front side of said absorber housing, as well as a guide plate;
    an anesthesia respiration system absorber mount, said guide plate being adapted to be pushed into said absorber mount;
    a centering notch provided on a front side of said guide plate in a direction of pushing in; and
    a centering pin, which engages the centering notch and fixes the guide plate in an end position, said centering pin being fastened to said absorber mount.

2. A device in accordance with claim 1, wherein the guide plate has another centering notch arranged offset from said centering notch by 180°.

3. A device in accordance with claim 1, wherein the guide plate has lateral surfaces with flattened portions along the direction of pushing in.

4. A device in accordance with claim 2, wherein the centering notches have wall surfaces, which have a wedge-shaped design and receive the centering pin.

5. A device in accordance with claim 2, wherein said centering pin has an upper part, which can perform a stroke movement and is under spring tension.

6. A device in accordance with claim 5, wherein locking grooves, at least partially receiving said upper part, are present at the centering notches.

7. A device in accordance with claim 6, wherein entry bevels for the upper part are arranged upstream of the locking grooves.

8. An anesthesia respiration system to absorber quick connection system, comprising:
    an absorber having an absorber housing, with a gas inlet opening concentrically arranged relative to a gas outlet opening on said absorber housing, and a guide portion;
    an anesthesia respiration system absorber mount, said guide portion being adapted to be pushed into said absorber mount;
    a centering notch provided on a front side of said guide portion with respect to a direction of pushing said guide portion into said absorber mount; and a centering pin, which engages the centering notch and fixes the guide plate in an end position, said centering pin being fastened to said absorber mount.

9. A connection system in accordance with claim 8, wherein the guide plate has another centering notch arranged offset from said centering notch by 180°.

10. A connection system in accordance with claim 8, wherein the guide plate has lateral surfaces with flattened portions along the direction of pushing in.

11. A connection system in accordance with claim 9, wherein the centering notches have wall surfaces, which have a wedge-shaped design and receive the centering pin.

12. A connection system in accordance with claim 9, wherein said centering pin has an upper part, which can perform a stroke movement and is under spring tension.

13. A connection system in accordance with claim 12, wherein locking grooves, at least partially receiving said upper part, are present at the centering notches.

14. A connection system in accordance with claim 13, wherein entry bevels for the upper part are arranged upstream of the locking grooves.

* * * * *